(12) United States Patent
Biedermann et al.

(10) Patent No.: US 8,257,400 B2
(45) Date of Patent: Sep. 4, 2012

(54) STABILIZATION DEVICE FOR THE DYNAMIC STABILIZATION OF VERTEBRAE OR BONES AND ROD LIKE ELEMENT FOR SUCH A STABILIZATION DEVICE

(75) Inventors: Lutz Biedermann, VS-Villingen (DE); Jürgen Harms, Karlsruhe (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 330 days.

(21) Appl. No.: 12/565,597

(22) Filed: Sep. 23, 2009

(65) Prior Publication Data
US 2010/0049254 A1   Feb. 25, 2010

Related U.S. Application Data

(63) Continuation of application No. 11/072,911, filed on Mar. 4, 2005, now Pat. No. 7,601,166.

(60) Provisional application No. 60/550,697, filed on Mar. 5, 2004.

(30) Foreign Application Priority Data

Mar. 5, 2004   (DE) .......................... 10 2004 010 844

(51) Int. Cl.
*A61B 17/70* (2006.01)
(52) U.S. Cl. ......... 606/265; 606/246; 606/254; 606/255
(58) Field of Classification Search .................. 606/246, 606/254, 255, 257, 261
See application file for complete search history.

(56) References Cited

U.S. PATENT DOCUMENTS

| | | | |
|---|---|---|---|
| 5,092,867 A | 3/1992 | Harms et al. | |
| 5,133,716 A | 7/1992 | Plaza | |
| 5,415,661 A | 5/1995 | Holmes | |
| 5,545,166 A * | 8/1996 | Howland | 606/264 |
| 6,248,106 B1 | 6/2001 | Ferree | |
| 6,440,169 B1 | 8/2002 | Elberg et al. | |
| 6,468,276 B1 | 10/2002 | McKay | |
| 6,488,682 B2 * | 12/2002 | Kikuchi et al. | 606/256 |
| 6,488,683 B2 * | 12/2002 | Lieberman | 606/263 |

(Continued)

FOREIGN PATENT DOCUMENTS

DE   101 17 1426 A1   10/2002

(Continued)

OTHER PUBLICATIONS

EP Search Report dated Jun. 2, 2005 for Application No. EP 05 00 3401.

*Primary Examiner* — Nicholas Woodall
(74) *Attorney, Agent, or Firm* — Christie, Parker & Hale, LLP (57) ABSTRACT

A stabilization device includes a first bone anchoring element, a second bone anchoring element, and a rod-shaped element for connecting the first and the second bone anchoring elements. The rod-shaped element includes a curved section, that undergoes an elastic deformation under the action of a force acting on the rod-shaped element via an anchoring element. The rod-shaped element and the anchoring elements are arranged so that deformation occurs when a force acts in a main direction of motion of bone parts or vertebra relative to each other, whereas a deformation is suppressed when a force acts in a direction that is essentially perpendicular to the main direction of motion.

11 Claims, 9 Drawing Sheets

U.S. PATENT DOCUMENTS

| | | |
|---|---|---|
| 6,616,669 B2 | 9/2003 | Ogilvie et al. |
| 6,626,909 B2 | 9/2003 | Chin |
| 6,949,123 B2 | 9/2005 | Reiley |
| 2002/0035366 A1 | 3/2002 | Walder et al. |
| 2002/0133155 A1 | 9/2002 | Ferree |
| 2003/0060823 A1 | 3/2003 | Bryan |
| 2003/0109880 A1 | 6/2003 | Shirado et al. |
| 2003/0191470 A1 | 10/2003 | Ritland |
| 2003/0220643 A1 | 11/2003 | Ferree |
| 2004/0015166 A1 | 1/2004 | Gorek |
| 2005/0203511 A1 | 9/2005 | Wilson-MacDonald et al. |
| 2005/0203516 A1 * | 9/2005 | Biedermann et al. ........... 606/61 |

FOREIGN PATENT DOCUMENTS

| | | |
|---|---|---|
| EP | 0 667 127 A1 | 2/1995 |
| EP | 1 188 416 A1 | 3/2002 |
| GB | 2 294 394 A | 5/1996 |
| WO | WO 02080787 A2 * | 10/2002 |
| WO | WO 02/102259 A2 | 12/2002 |

* cited by examiner

STABILIZATION DEVICE FOR THE DYNAMIC STABILIZATION OF VERTEBRAE OR BONES AND ROD LIKE ELEMENT FOR SUCH A STABILIZATION DEVICE

REFERENCE TO EARLIER FILED APPLICATIONS

This application is a continuation of application Ser. No. 11/072,911 filed Mar. 4, 2005, now U.S. Pat. No. 7,601,166 which claimed the benefit of the filing date under 35 U.S.C. §119(e) of Provisional U.S. Patent Application Ser. No. 60/550,697, filed Mar. 5, 2004, which is hereby incorporated by reference. The present application also claims foreign priority benefits pursuant to 35 U.S.C. §119(a)-(d) for German Patent Application 10 2004 010 844.7, filed Mar. 5, 2004, in Germany.

BACKGROUND

The present invention relates to a stabilization device for the dynamic stabilization of vertebrae or bones, and a rod-like element used in this stabilization device.

European Patent Application, EP 1 188 416 A1, discloses a dynamic stabilization device for stabilizing neighboring thoracic vertebra. The device comprises two pedicle screws and a cable-like strap (31), which is attached to the receiving part of the pedicle screw by a clamping screw. The device also contains a support element (3) in the form of a pressure-resistant body that is mounted on the strap.

U.S. Patent Publication 2003/0109880 A1 describes a dynamic stabilization device for vertebrae which comprises a first and a second screw to be anchored in a vertebra. A coil spring (11) connects an upper portion of the first screw and the upper portion of the second screw.

U.S. Pat. No. 5,415,661 describes an implantable spinal assist device which includes a body composed of a composite material made up of a fiber material interspersed in a matrix material. The body is curved along its longitudinal axis and comprises a curved center section unattached to a motion segment unit and a pair of opposed terminal sections. Similarly, U.S. Patent Publication 2003/0191470 A1 discloses a dynamic fixation device. The device includes a flexible portion and two ends that are adapted for connection to pedicle screws. In both of these references, the curved elastic rod, which is anchored at its ends on neighboring vertebrae on the same side of the spinal column by means of anchoring elements with a shaft of the pedicle screws. Therefore, the curved elastic rods face in the anterior/posterior direction. The curvature fulfils the function of a spring rod.

The known stabilization devices each use two of these stabilization devices for stabilizing two neighboring vertebrae with the stabilization devices being anchored to the right and to the left of the middle longitudinal axis of the spinal column.

U.S. Pat. No. 6,440,169 B1, describes a stabilization device for the spinal column, which comprises an elastic body in the form of a leaf spring which extends between anchoring points in neighboring vertebrae and is shaped such that it forms the wall of an orifice, whereby the orifice faces in the anterior/posterior direction with respect to the body of the patient and is closed in the medial/lateral direction.

Figure 8A:
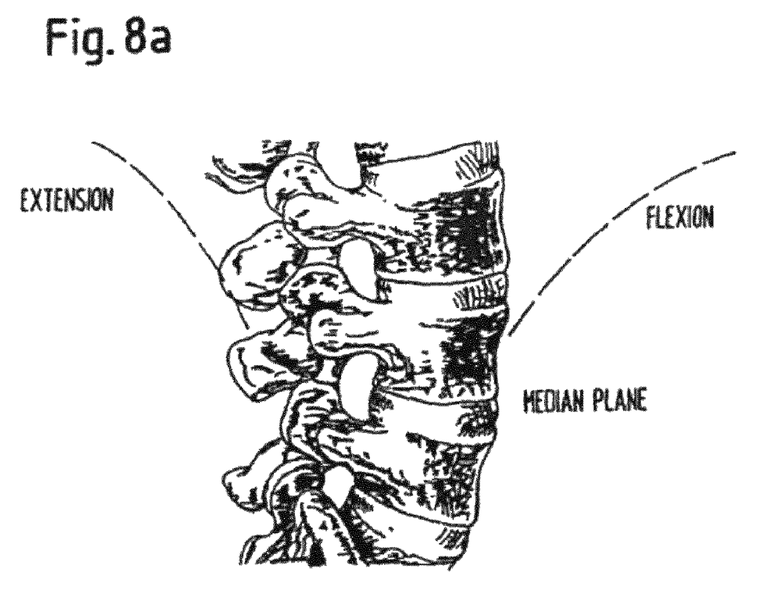
FIG. 8a shows a section of the spinal column viewed from the side in flexion and extension.
Figure 8B:
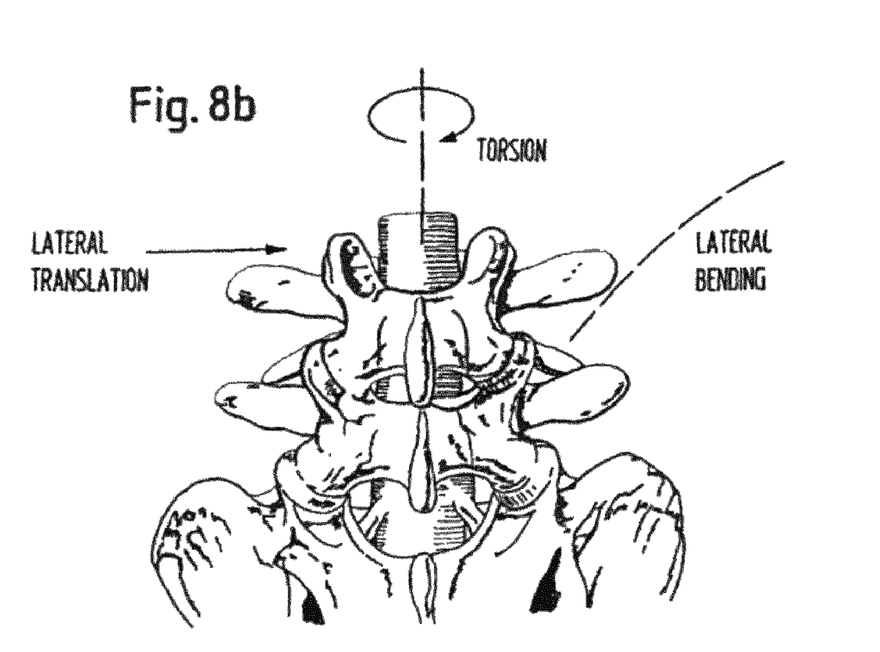
FIG. 8b shows a section of the spinal column viewed from behind, showing lateral translation motion as well as torsional motion around the longitudinal axis of the spinal column.

It is it is desirable to support the disk in a defined fashion with respect to the transmitted forces and to control the motion by means of a posterior dynamic stabilization device, especially in the presence of a damaged or an artificial intervertebral disk. In this regard, a flexion and an extension of the spinal column or of the element containing the respective intervertebral disk, as shown in FIG. 8a, is desired, whereas lateral translational motion as well as a torsional motion around the middle longitudinal axis of the spinal column, as shown in FIG. 8b, is undesired.

BRIEF SUMMARY

It is therefore the object of the present invention to provide a dynamic stabilization device for stabilizing and limiting the motion of neighboring vertebrae or bones, which device is simple in design and permits a limited degree of flexion and extension yet prevents lateral translational motion and a rotational motion of the vertebrae or bones relative to each other.

The present invention comprises a stabilization device with a first bone anchoring element, a second bone anchoring element and a rod shaped element for connecting the first bone anchoring element and the second bone anchoring element which comprises a curved section that undergoes elastic deformation under the action of a force acting on a rod shaped element via the bone anchoring element.

The present invention also comprises a stabilization device with a first bone anchoring element, a second bone anchoring element, a third bone anchoring element, a fourth bone anchoring element, a first rod-shaped element that is connect to the first or second bone anchoring element and to the third or fourth bone anchoring element and a second rod-shaped element that is connected to the second or first bone anchoring element and to the fourth or third bone anchoring element, whereby the points of connection of the bone anchoring elements to the rod-shaped elements define a plane and the rod-shaped elements each comprise a curved section which undergoes an elastic deformation under the action of a force acting on the rod-shaped element via an anchoring element and wherein the rod-shaped elements are arranged so that the curved section resides within the plane or is parallel to the plane defined by these various components.

The present invention also comprises a dynamic stabilization device for having a first bone anchoring element, a second bone anchoring element, and a rod-shaped element that can be connected to the first and to the second bone anchoring element, whereby the rod-shaped element includes a curved section (7) between the first and second bone anchoring elements, which undergoes an elastic deformation under the action of a force acting on the rod-shaped element via the anchoring element; and wherein the curved section, in the operational state of the stabilization device, resides within a plane that is essentially perpendicular to the median plane of the human body.

The invention is advantageous in that a desired limitation of motion can be achieved in a simple fashion by selecting suitably dimensioned rod-shaped elements. Moreover, the rod-shaped elements of the present invention are easy to manufacture. Furthermore, the stabilization device can also be used with artificial intervertebral disks.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

DETAILED DESCRIPTION OF THE DRAWINGS AND PRESENTLY PREFERRED EMBODIMENTS

The invention and various embodiments thereof are presented in FIGS. 1 to 7 and the accompanying descriptions wherein like numbered items are identical.

Figure 1:
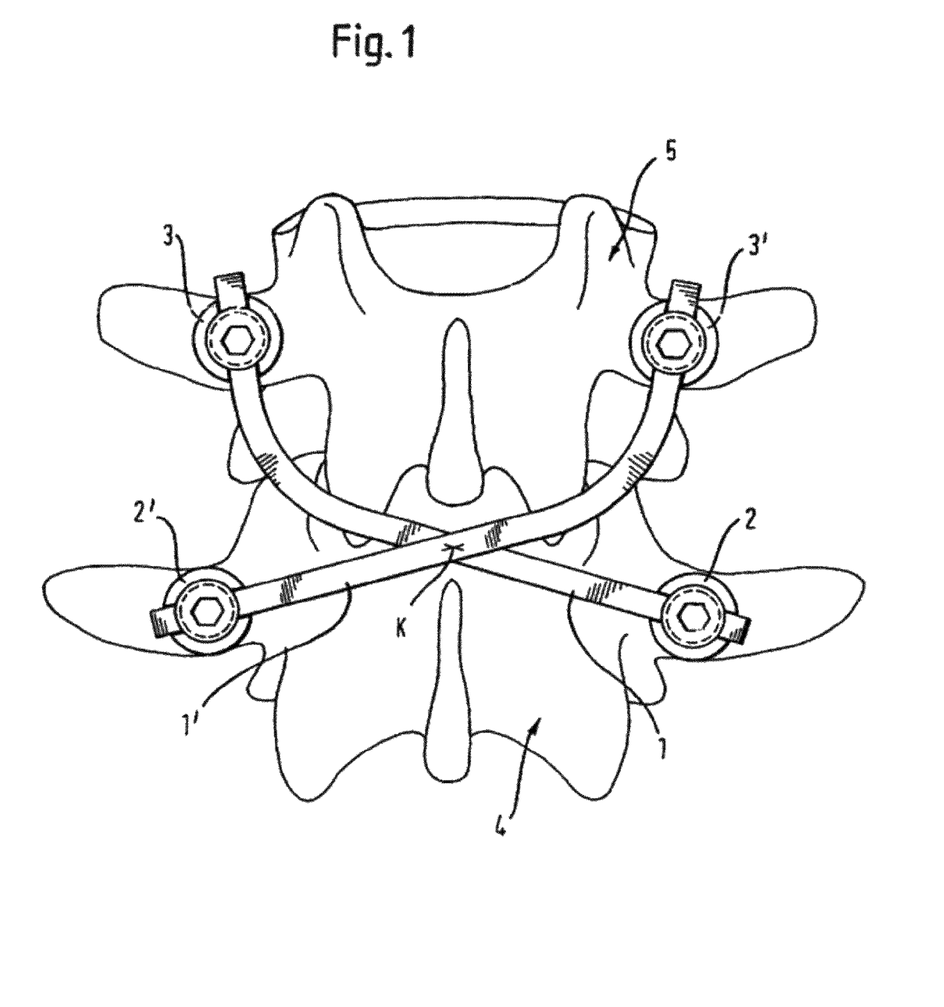
FIG. 1 shows a top view of the stabilization device according to a first embodiment of the invention viewed from the posterior side of the spinal column.

As is seen in FIG. 1, the stabilization device comprises a first and a second rod-shaped element, 1, 1'. These two rod-shaped elements are each connected to two bone anchoring elements, which are anchored in the pedicles of two neighboring vertebrae, 4, 5. In this particular example, pedicle screws are used as the bone anchoring elements. The first pedicle screw 2 of rod-shaped element 1 is anchored to the right pedicle of the lower vertebra, 4, whereas the second pedicle screw, 3, of rod-shaped element 1 is anchored to the left pedicle of the upper vertebra, 5. Symmetrical to this arrangement, the first pedicle screw, 2', of rod-shaped element 1' is anchored to the left pedicle of the lower vertebra, 4, whereas the second pedicle screw, 3', of rod-shaped element 1' is anchored to the right pedicle of the upper vertebra 5. In this embodiment, the rod-shaped elements, 1, 1', intersect at a point, K, within the plane of symmetry M (shown in FIG. 6b).

Figure 2A:
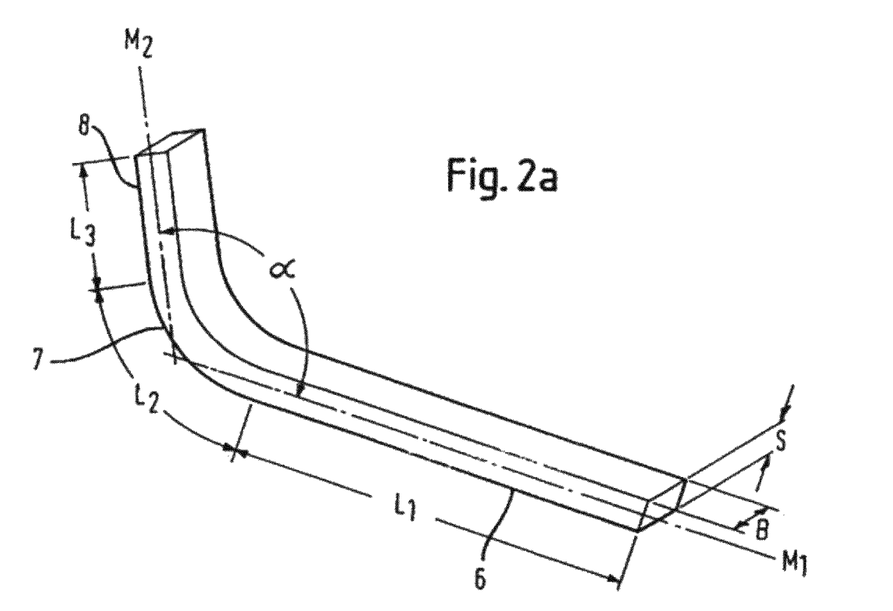
FIG. 2a shows a perspective view of a rod-shaped element of the stabilization device according to FIG. 1.

The first rod-shaped element, 1, is in the form of a curved rod with a rectangular cross-section as seen in FIG. 2a. Rod-shaped element 1 comprises a first straight section, 6, of length L1, and, adjacent to it, a curved section, 7, of length L2, and, adjacent to it, another straight section 8 of length L3. The middle longitudinal axes, M1 and M2, of the straight sections intersect and form an obtuse angle, α. In the embodiment shown, the length, L1, of the first straight section, 6 is approximately three times the length, L3, of the second straight section, 8. The rod-shaped element has a broad side, B, and a narrow side, S. The curvature extends over the broad side, B, of the rod-shaped element. The flexural strength due to a force acting perpendicular to the broad side, B, of the rod-shaped element is smaller than the flexural strength due to a force acting perpendicular on its narrow side, S. Moreover, due to the lever effect resulting from the difference in the lengths, L1 and L3, of the straight sections, 6, 8, the flexural strength of the rod-shaped element with respect to a force acting perpendicularly to the rod-shaped element on the long section, 6, is smaller than the flexural strength with respect to a force acting on the end of the short section, 8, in an orthogonal direction.

The rod-shaped element thus possesses oriented flexural strength that can be adjusted during the manufacture as desired by selecting the cross-section, curvature, and length of the rod-shaped element to achieve the desired properties.

The rod-shaped element 1 can be made from a body-compatible materials, preferably from one piece of such material. The body compatible material comprises stainless steel, titanium alloys, nickel-titanium alloys, nitinol, chrome alloy, cobalt chrome alloys, shape memory alloys, materials with super elastic properties, carbon reinforced composites, silicone, polyurethane, polyester, polyether, polyalkene, polyethylene, polyamide, poly(vinyl) fluoride, polyetheretherketone (PEEK), or polytetrafluoroethylene (PTFE).

In its simplest embodiment, the second rod-shaped element, 1', is attached in mirror-like symmetry to the first rod-shaped element, 1, such that the curved sections face in opposite directions.

Figure 2B:
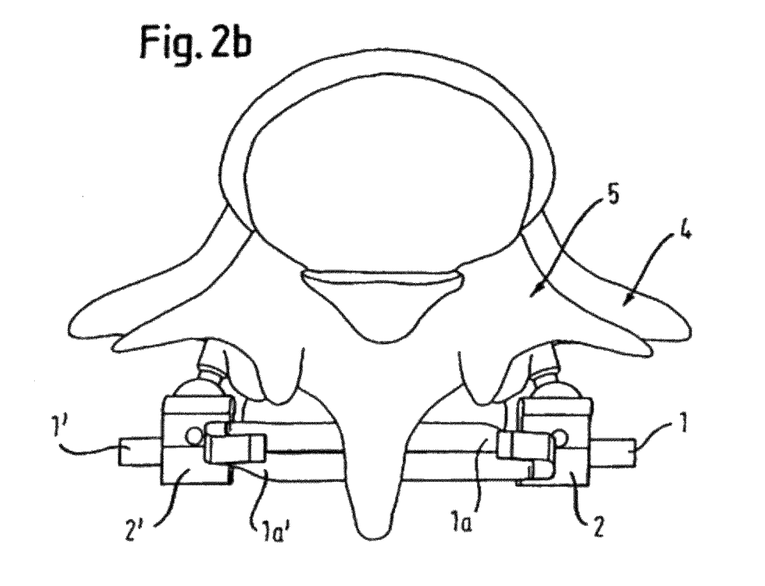
FIG. 2b shows a perspective view of the stabilization device according to FIG. 1 viewed from above with a preferred implementation of the rod-shaped elements (the upper two bone anchoring elements not shown)

FIG. 2b shows the stabilization device of FIG. 1 from above with a preferred implementation of rod-shaped elements, 1, 1'. In this FIG. 2b, the respective upper bone anchoring elements are not shown. In an area, 1a, 1a', adjacent to the section with which they are anchored in the anchoring element, rod-shaped elements 1, 1' are curved to extend out of the plane defined by the connection points so that they are guided past each other without interfering with each other in the operational state of the stabilization device. This configuration enables all the connection points of the bone anchoring elements of the rod-shaped elements to reside in a plane that is orthogonal to the median plane indicated in FIG. 8a.

Figure 2C:
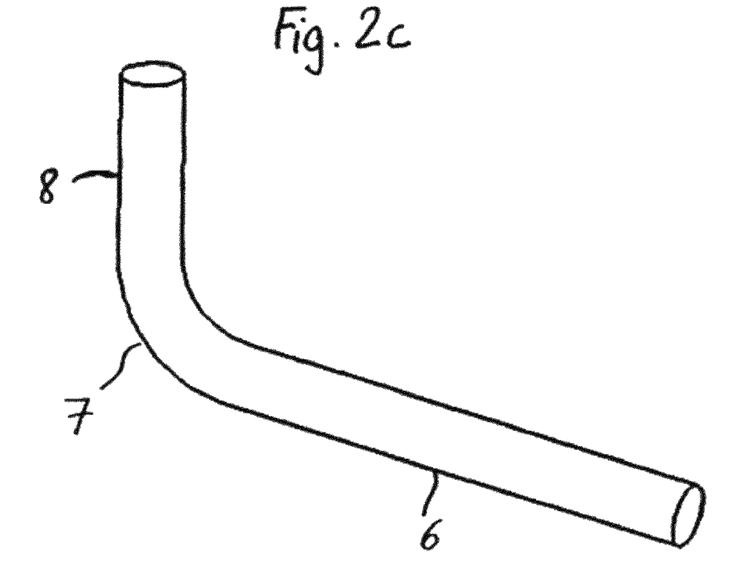
FIGS. 2c and 2d show a perspective view of modifications of the rod-shaped element to be used in the stabilization device according to FIG. 1.
Figure 2D:
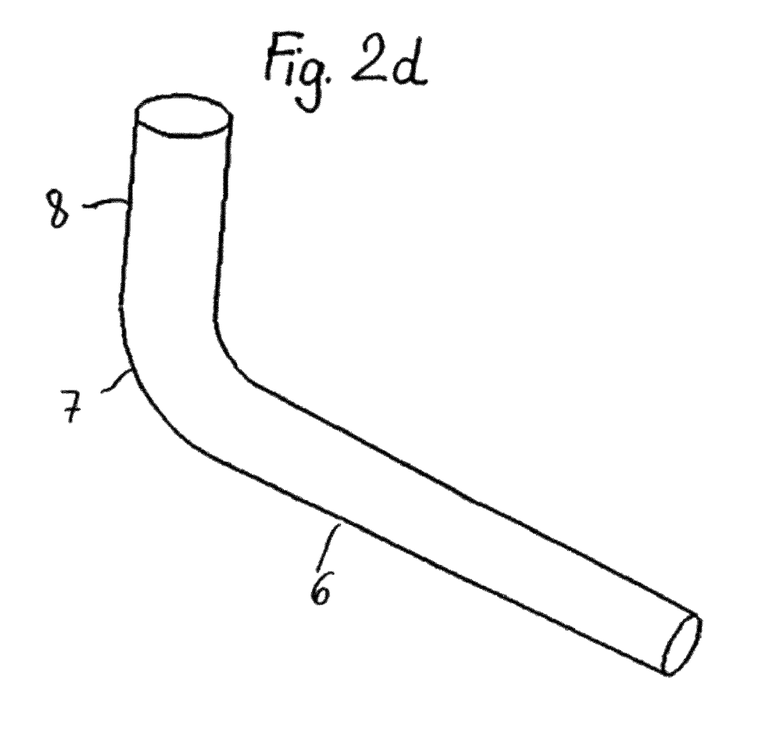

FIG. 2c shows a modification of the rod-shaped element which can be used in the stabilization device of FIG. 1. The rod-shaped element according to FIG. 2c differs from the rod-shaped element shown in FIG. 2a because the cross-section is spherical, instead of rectangular. As is shown in FIG. 2d, the diameter of the rod-shaped element may vary. For example, it can increase from the free end of the first straight section 6 towards the free end of the second straight section 8.

Figure 3:
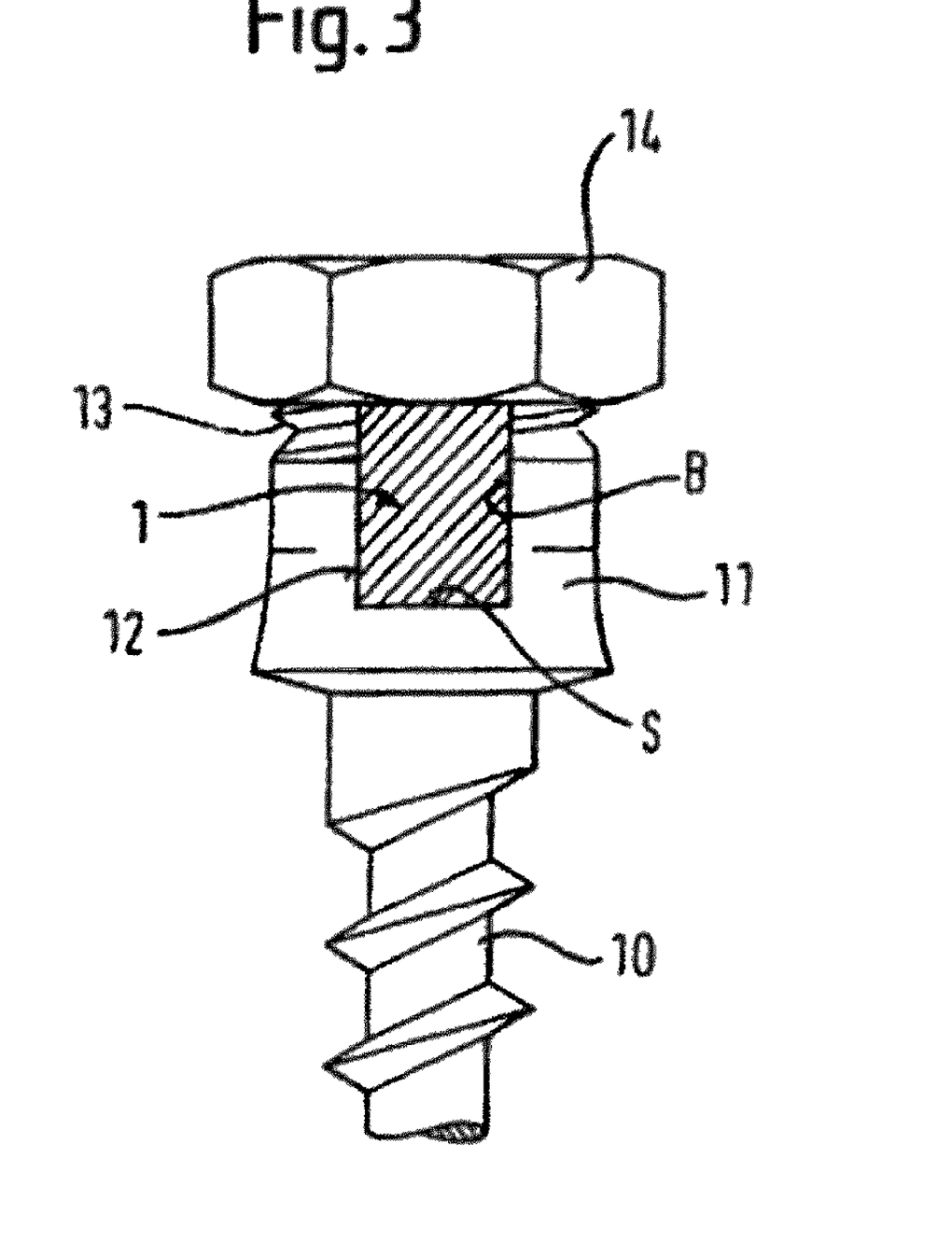
FIG. 3 shows a partial sectional view of an anchoring element for anchoring the rod-shaped element of FIG. 2 according to a first embodiment.

As is shown in FIG. 3, in a first embodiment, the rod-shaped element, 1, 1', is fixed in a monoaxial pedicle screw. This screw comprises a threaded shaft, 10, with a bone thread and a receiving part, 11, that is rigidly connected thereto. Receiving part 11 is provided to be essentially cylindrically symmetrical in shape and includes a recess, 12, which extends from its free end facing away from threaded shaft 10. The receiving part 11 has a rectangular cross-section that is dimensioned so that rod-shaped element 1, 1' can be placed therein and still remain capable of shifting in the direction of its longitudinal axis. The narrow side, S, of rod-shaped element 1 rests in the base of the recess 12 of the receiving part. The receiving part also includes an external thread, 13, that extends from its free end and has a pre-determined length which is dimensioned such that, when the rod-shaped element inserted, the external thread extends to below the upper side thereof. A nut, 14, that can be screwed onto the external thread 13 is provided for fixing the rod-shaped element in the receiving part.

Figures 4, 5:
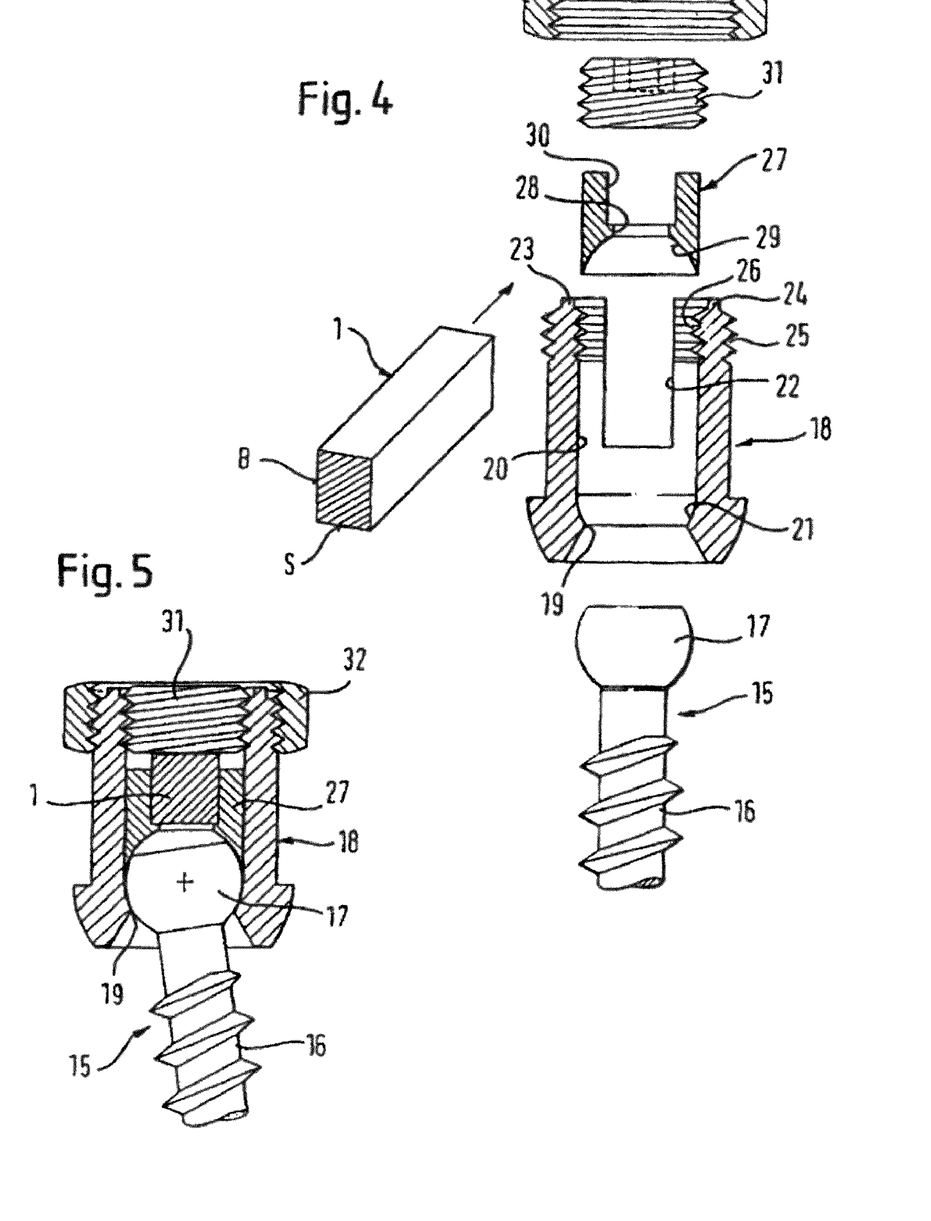
FIG. 4 shows a partial sectional exploded view of an anchoring element for anchoring the rod-shaped element of FIG. 2 according to a second embodiment.
FIG. 5 shows a partial sectional view of the anchoring element of FIG. 4 connected to a rod-shaped element.

In a further embodiment, a polyaxial screw is used as the bone anchoring element for connecting to the rod-shaped element, 1, 1', is as shown in FIGS. 4 and 5. This polyaxial screw comprises a screw element, 15, with a threaded shaft, 16, with a bone thread, and a spherical segment-shaped head, 17, with a recess for screwing-in (not shown). Furthermore, a receiving part, 18, that can be connected to screw element 15 is shown. The screw element 15 pivots relative to the receiving part 18. The receiving part 18 is provided to be essentially cylindrical in shape and comprises at its one end a first bore, 19, that is aligned axially with the screw element 15. The first bore 19 has a diameter that is smaller than that of head 17 of the screw element 15. Receiving part 18 further comprises a coaxial second bore, 20, that is open on its end opposite to first bore 19 and whose diameter is sufficiently large to enable the screw element, 15, to be guided through the open end with its threaded shaft through first bore 19 and with head 17 to the base of second bore 20. A spherically shaped section or a ledge, 21, is provided in the receiving part for abutment of head 17 between the first bore, 19, and the second bore, 20. It will be appreciated by those skilled in the art that any shaped structure can be used provided that it holds the head of the screw element in the bore.

The receiving part 18 further comprises a recess 22, which is arranged symmetrically with respect to the middle of the receiving part and has a rectangular cross-section for receiving the rod-shaped element, 1, 1', and through which two free legs, 23, 24, are formed. In an area on the receiving part 18, adjacent to the free end, legs 23, 24, there may be an external thread, 25, and an internal thread, 26.

In addition, the polyaxial screw may include a pressure element, 27, that is capable of pressing onto the head 17 of the screw. Pressure element 27 comprises a coaxial bore, 28, for insertion of a screw driver on one side, and, at its side facing head 17, a spherical recess, 29, for receiving the receiving head 17. At its side facing away from the head, pressure element 27 comprises a recess, 30, with a rectangular cross-section for receiving the rod-shaped element, 1, 1'. The width of recess 30 is just slightly larger than the narrow side, S, of rod-shaped element 1, 1' such that the rod-shaped element can be introduced with its narrow side, S, towards the base of the recess so that it is capable of shifting in longitudinal direction within the recess. The depth of recess 30 is preferably slightly smaller than height B of the rod-shaped element. Although shown in this manner, it will be appreciated by those skilled in the art that the pressure element can be of other shapes so long as it is capable of pressing onto the head of the screw.

Moreover, an internal screw 31 can be screwed onto the legs 23, 24 for fixing rod-shaped element 1, 1' in the receiving part as well as for fixing the angle position of screw element 15 relative to the receiving part. A nut 32 can be screwed onto the outside of legs 23, 24 to secure the receiving part 18.

In operation, the pedicle screws, 2, 3, 2', 3', are first screwed into the vertebrae, 4, 5, to be connected by the stabilization device. In the case of the monoaxial screws shown in FIG. 3, the threaded shafts, 10, are screwed in until the receiving parts, 11, of the pedicle screws, 2, 3 or 2', 3' to be connected to a rod-shaped element 1, 1' are aligned with respect to each other such that the rod-shaped element can be introduced without jamming. The rod-shaped element is then inserted into the receiving part and fixed into the receiving part by screwing-on nut 14.

In the case of the polyaxial screws, shown in FIGS. 4 and 5, screw element 15 is first inserted into receiving part 18, then followed by the pressure element 27. Then the screw element 15 is screwed into the pedicle as described above. Subsequently, the rod-shaped element 1 or 1' is inserted into the receiving part. Due to the flexible connection between the head 17 and receiving part 18, the receiving parts 18 of two pedicle screws 2, 3 or 2', 3' to be connected by the rod-shaped element, 1 or 1', align themselves correctly with respect to the rod, which is of advantage in the intersecting arrangement of the rod-shaped elements. Subsequently, the receiving parts are fixed relative to the head and the rod by means of the internal screw and the nut.

Figure 6A:
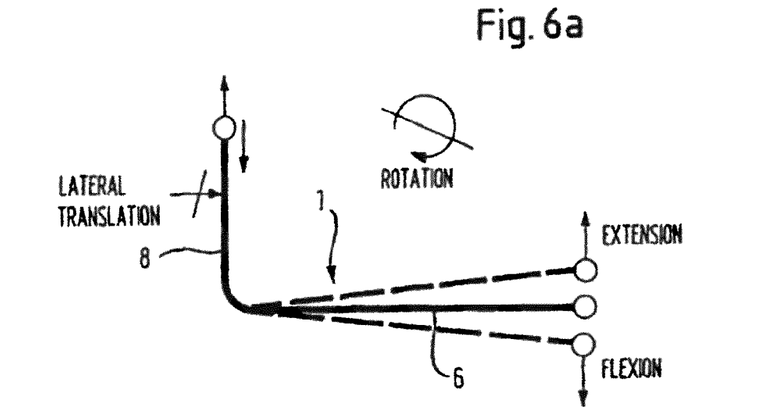
FIG. 6a shows a schematic illustration of the mobility of a rod-shaped element of the stabilization device of FIG. 1.
Figure 6B:
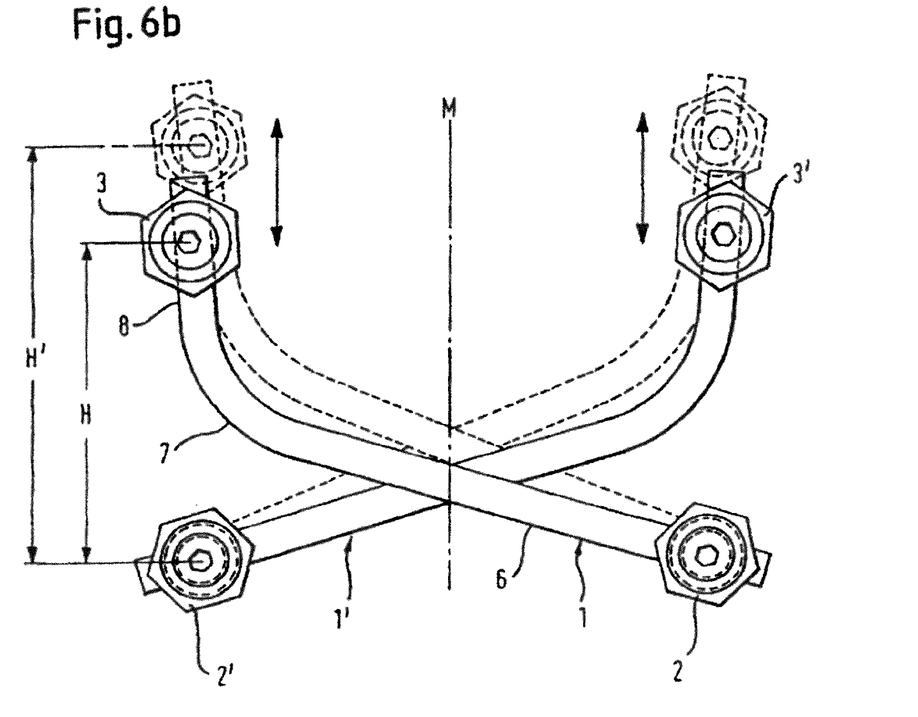
FIG. 6b shows a schematic illustration of the function of the stabilization device according to the first embodiment.

FIGS. 6a and 6b show a schematic illustration of the function of the stabilization device. The rod-shaped element 1 shown in FIG. 6a with no load can be likened to an angle lever with a long lever arm, 6, and a short lever arm, 8. In the presence of load due to flexion or extension of the spinal column segment, a small force component acting on the anchoring points orthogonal to long lever arm 6 leads to the elastic deformation of rod-shaped element 1, by displacing the long lever arm and increasing or reducing the size of the radius of curvature relative to the resting position upon flexion or extension, respectively.

The continuous lines and the dashed lines in FIG. 6b show rod-shaped elements, 1, 1', in a first state and in a second state, respectively, with the latter corresponding to a flexion of the spinal column segment. In the first state, pedicle screws 2', 3, to which rod-shaped element 1 is connected, are at a distance, H, from each other in the direction of the middle longitudinal axis of the spinal column. Flexion of the spinal column segment leads to the bending of rod-shaped element 1, whereby the radius of curvature increases and therefore the distance between the pedicle screws from each other in the direction of the middle longitudinal axis increases to H'. In contrast, an extension of the spinal column segment causes the radius of curvature of the rod-shaped elements to decrease. This causes the distance between the pedicle screws to decrease. (not shown).

When a force component acts perpendicularly to the short lever arm, it is more difficult or even impossible for the curvature of the rod-shaped elements to change because a greater force is required. This prevents a lateral translational motion. Due to the elongated implementation of the rod-shaped elements, there is also a high degree of rotational stability with respect to a rotational motion of the vertebrae relative to each other.

Figure 6C:
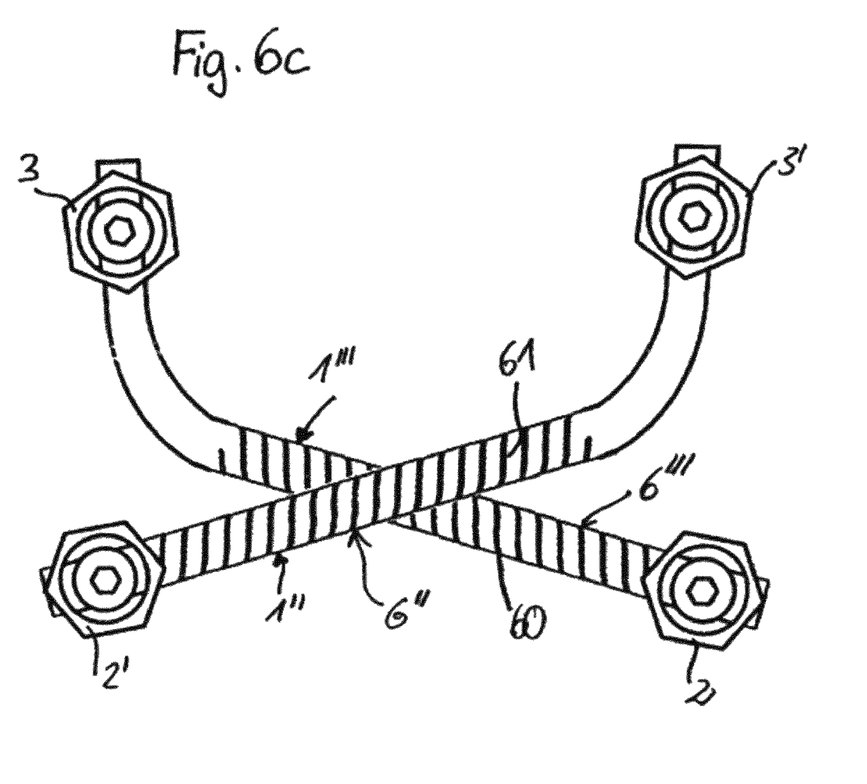
FIG. 6c shows a modification of the stabilization device according to the first embodiment.

FIG. 6c shows a modification of the stabilization device according to FIG. 1. Instead of rigid rod-shaped elements 1, 1' rod-shaped elements 1", 1''' are used which have a spring-like flexible section 6", 6'''. Preferably the spring-like section 6", 6''' is the longer straight section. Flexibility is achieved, e.g. by a helical recess 60 creating helical spring-like windings 61. The rod-shaped element may be hollow. The spring-like section can be achieved with another construction.

Figure 7:
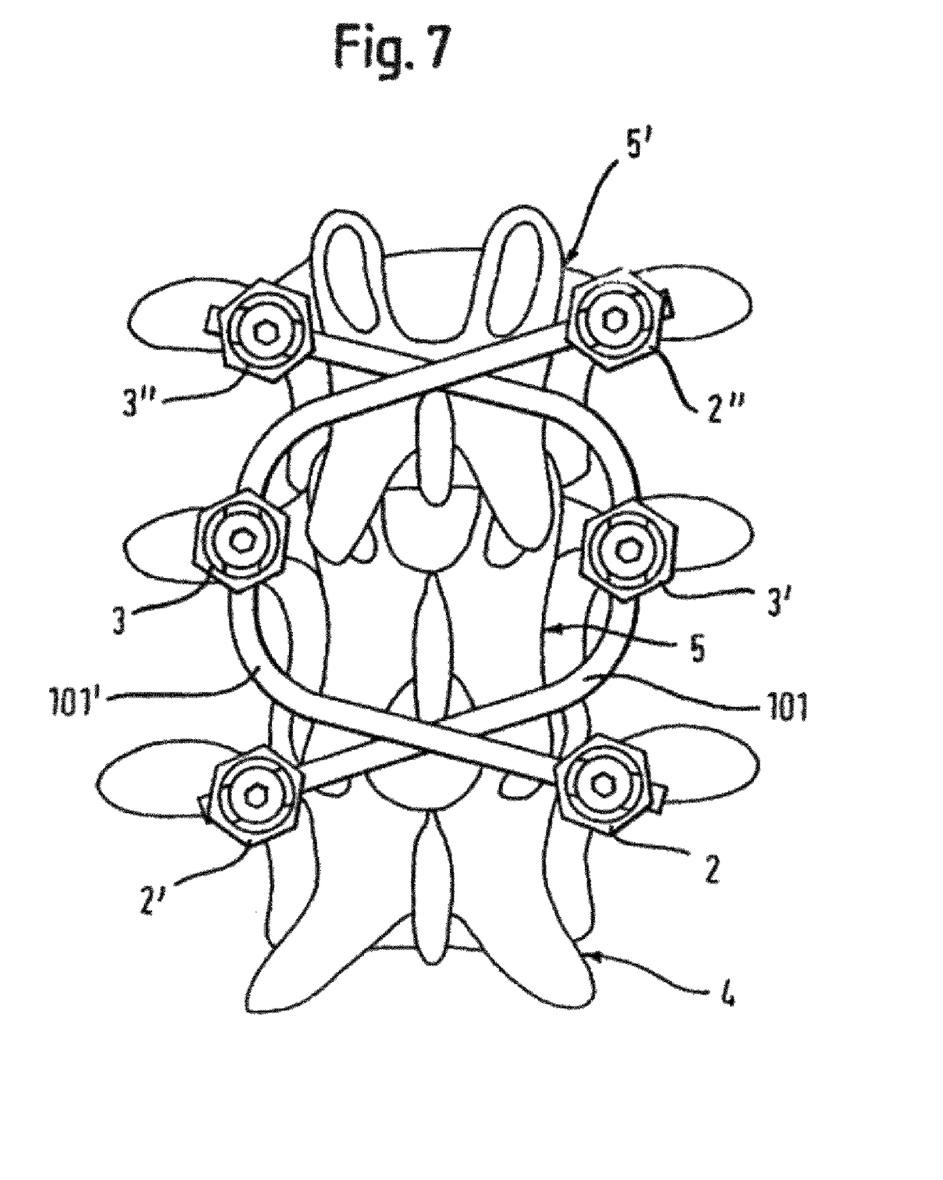
FIG. 7 shows a modification of the stabilization device of the first embodiment.

FIG. 7 shows a second embodiment of the instant invention. The stabilization device of this embodiment comprises to two motion elements, that extend between three vertebrae, 4, 5 and 5'. This embodiment comprises rod-shaped elements, 101, 101', whose shape is "u-shaped." That is the rod-shaped element is identical to that generated by mirroring a rod-shaped element, 1, 1', according to the first embodiment on a plane that stands orthogonal on the free end of the short section. Rod-shaped elements 101, 101' each are anchored at their ends in the pedicles on the same side of the spinal column by means of pedicle screws 2, 2" or 2', 3", between two vertebra, 4, 5' which have a intermediate vertebrae 5 between them. The middle sections of the rod-shaped elements 101 and 101' are also anchored in the pedicles of the intermediate vertebra 5 on the opposite side of the spinal column by means of pedicle screws 3 or 3'. The rod-shaped elements 101 and 101' can be constructed from a unitary rod or from multi-segments which are joined together to form a unitary rod structure.

Modifications of the embodiments described above are also possible. For example, the lengths of the individual sections of the rod-shaped elements can be selected according to the dimensions of the vertebrae to be connected. The invention is not limited to the rod-shaped elements of the stabilization devices of the first embodiment comprising a long and a short straight section. There can also be only one long and one curved section. In the stabilization device according to the second embodiment, the straight sections can differ in length, however in this embodiment it is important that the rod-shaped element is curved between the one attachment point and the other attachment point so that the rod-shaped element effects a change in the distance of the attachment points under the action of flexural moments.

Moreover, the features of the various embodiments described above can be combined with each other. The stabilization device according to the first embodiment can also comprise rod-shaped elements with a circular cross-section. A square cross-section shall also be possible, though this reduces one degree of freedom in the selection of the flexural-elastic properties of the rod-shaped element.

Instead of the monoaxial screws and polyaxial screws described above, monoaxial screws and polyaxial screws can be used, in which the fixation of the head or the rod occurs by different means. Hooks may also be used for fixation of the rod-shaped element.

Although the drawing and descriptions describe the stabilization device for the spinal column, the invention should not be so limited. The instant invention can also be used to stabilize bones.

The embodiments described above and shown herein are illustrative and not restrictive. The scope of the invention is indicated by the claims, including all equivalents, rather than by the foregoing description and attached drawings. The invention may be embodied in other specific forms without departing from the spirit and scope of the invention.

We claim:

1. A stabilization device for the dynamic stabilization of vertebrae or bones, comprising:
   a first bone anchoring element for anchoring in a first bone part or vertebra;
   a second bone anchoring element for anchoring in a second bone part or vertebra;
   a third bone anchoring element for anchoring in a third bone part or vertebra;
   a generally U-shaped rod comprising a first generally straight end portion having a free end, a second generally straight end portion having a free end, and a curved portion between the first and second generally straight end portions;
   wherein the entire rod from the free end of the first generally straight end portion to the free end of the second generally straight end portion is generally U-shaped;
   wherein the first bone anchoring element is attached directly to the first generally straight end portion;
   wherein the second bone anchoring element is attached directly to the second generally straight end portion;
   wherein the third bone anchoring element is attached directly to the curved portion between the first and second generally straight end portions; and
   wherein the curved portion elastically deforms when a force acts on the rod by any one of the first bone anchoring element and second bone anchoring element.

2. A stabilization device according to claim 1, wherein the first and the third bone anchoring elements are arranged diagonally opposite from each other relative to a main direction of motion and wherein the second and the third bone anchoring elements are arranged diagonally opposite from each other relative to the main direction of motion.

3. A stabilization device according to claim 1, wherein said stabilization device further comprises fourth, fifth and sixth bone anchoring elements and a second generally U-shaped rod connecting the fourth, fifth and sixth bone anchoring elements, said fourth, fifth and sixth bone anchoring element with said second rod being arranged symmetrically to the first, second and third bone anchoring elements with the generally U-shaped rod.

4. A stabilization device according to claim 3, wherein said generally U-shaped rod and said second said second generally U-shaped rod each intersect the plane of symmetry at least once.

5. A stabilization device according to claim 1, wherein the U-shaped rod has a rectangular cross-section.

6. A stabilization device according to claim 1, wherein the U-shaped rod has a square cross-section.

7. A stabilization device according to claim 1, wherein the U-shaped rod has a circular cross-section.

8. A stabilization device according to claim 1, wherein the first bone anchoring element comprises an anchoring section for anchoring in a bone and a receptacle connected thereto which has a recess having a cross-section, wherein the recess cross-section matches the cross-section of the U-shaped rod.

9. A stabilization device according to claim 8, wherein the anchoring section is rigidly connected to the receptacle.

10. A stabilization device according to claim 8, wherein the anchoring section and the receptacle have opposed contacting surfaces that move relative to each other to permit pivoting.

11. A stabilization device according to claim 1 wherein the first and second generally straight end portions converge toward the curved portion to a location adjacent the third bone anchoring element.

* * * * *